United States Patent [19]

Fujii et al.

[11] Patent Number: 4,652,570

[45] Date of Patent: Mar. 24, 1987

[54] ANTI-CANCER COMPOSITION FOR DELIVERING 5-FLUOROURACIL

[75] Inventors: Setsuro Fujii, Toyonaka; Norio Unemi; Setsuo Takeda, both of Tokushima, all of Japan

[73] Assignee: Taiho Pharmaceutical Company, Limited, Tokyo, Japan

[21] Appl. No.: 645,165

[22] Filed: Aug. 28, 1984

Related U.S. Application Data

[60] Division of Ser. No. 212,543, Dec. 3, 1980, Pat. No. 4,481,203, which is a division of Ser. No. 15,161, Feb. 13, 1979, Pat. No. 4,328,229, which is a continuation-in-part of Ser. No. 891,343, Mar. 29, 1978, abandoned.

[30] Foreign Application Priority Data

Apr. 5, 1977 [JP] Japan ................................ 52-39341
Feb. 10, 1978 [JP] Japan ................................ 53-14676

[51] Int. Cl.$^4$ ............................................. A61K 31/505
[52] U.S. Cl. .................................................... 514/274
[58] Field of Search ......................... 424/251; 514/274

[56] References Cited

PUBLICATIONS

Burchenal et al., Cancer Chemotherapy Repts., 6, pp. 1–5 (1960).
Jato et al., J. of Pharm. Sciences, 62, pp. 1975–1978 (Dec. 1978).
Jato et al., J. of Pharm. Sciences, 64, pp. 943–946 (Jun. 1975).

*Primary Examiner*—Jerome D. Goldberg
*Attorney, Agent, or Firm*—Murray and Whisenhunt

[57] ABSTRACT

An anti-cancer composition for treating cancers sensitive to 5-fluorouracil therapy in warm-blooded animals, comprising 5-fluorouracil and uracil.

6 Claims, No Drawings

ANTI-CANCER COMPOSITION FOR DELIVERING 5-FLUOROURACIL

This is a divisional application of Ser. No. 212,543, filed Dec. 3, 1980, now U.S. Pat. No. 4,481,203, which is a division of application Ser. No. 015,161, filed Feb. 13, 1979, now U.S. Pat. No. 4,328,229, a continuation-in-part of application Ser. No. 891,343, filed Mar. 29, 1978, now abandoned.

This invention relates to anti-cancer compositions for treating cancers sensitive to 5-fluorouracil therapy in warm-blooded animals.

In recent years, various excellent anti-cancer compositions have been introduced into use for the chemotherapy of malignant cancers with progressively improved results. Chemotherapeutic effects so far achieved nevertheless still remain temporary and are not always satisfactory in completely inhibiting the proliferation of cancerous tissues and enabling patients to survive a long period of time. The anti-cancer compositions frequently used for clinical purposes at present are predominantly those consisting essentially of a 5-fluorouracil, and various 5-fluorouracils will be developed in the future. However, anti-cancer compositions comprising a compound having a 5-fluorouracil as its skeleton and serving as the active component thereof have both merits and demerits. For example, 5-fluorouracil, although highly effective, has high toxicity and marked side effects. Accordingly, when administered, the compound produces a therapeutic effect and, at the same time, inevitably gives side effects. Further 1-(2-tetrahydrofuryl)-5-fluorouracil, which has relatively lower toxicity and reduced side effects, is said to be slightly inferior in its anti-cancer effect. In view of these situations, it has been expected to develop more advantageous 5-fluorouracils.

On the other hand, research has been conducted to provide increased anti-cancer efficacies by improving the method or mode of administering anti-cancer compositions which are conventionally used. For example, attempts have been made to use a known anti-cancer agent conjointly with another drug with or without anti-cancer activity to thereby achieve an increased therapeutic efficacy with reduced side effects. The known compositions of this type, nevertheless, are not fully effective for the chemotherapy of malignant cancers.

Compounds containing 5-fluorouracil as the skeleton thereof are thought to exhibit an anti-cancer effect when converted to 5-fluorouracil in the living body. It appears that they generally fail to give a high anti-cancer effect because the resulting 5-fluorouracil is promptly metabolized and thereby inactivated. Accordingly it is desired that the 5-fluorouracil in the living body be prevented from inactivation by some expedient, preferably in such a manner that the 5-fluorouracil present in the cancer tissues will remain active, whereas the 5-fluorouracil present in the normal tissues can be inactivated.

The object of this invention is to provide anti-cancer compositions for treating cancers sensitive to 5-fluorouracil in warm-blooded animals, comprising 5-fluorouracil and uracil, having a high anti-cancer effect and which suppress toxicity and side effects.

This invention provides anti-cancer compositions for delivering 5-fluorouracil to cancer tissues sensitive to 5-fluorouracil therapy in warm-blooded animals, said composition comprising a pharmaceutically effective amount of 5-fluorouracil (a) and an effective amount of uracil (b).

Although uracil (b) itself has no anti-cancer effect whatever, the use of 5-fluorouracil (a) in combination therewith according to this invention produces a greatly enhanced anti-cancer effect, resulting in a therapeutic index of about 1.6 to 4.1 times that of the 5-fluorouracil alone. With the anti-cancer composition of this invention administered, cancer tissues have an exceedingly increased 5-fluorouracil concentration, whereas the other tissues, such as the blood serum, will exhibit little or no increase in the concentration of 5-fluorouracil. This shows that the present composition is in ideal therapeutic agent for cancers sensitive to 5-fluorouracil therapy in warm-blooded animals.

The compound 5-fluorouracil (compound 1) is disclosed in Japanese Published Examined Patent Application No. 3873/1961.

The amount of uracil (b) to be used relative to the 5-fluorouracil (a) for the preparation of the anti-cancer compositions according to this invention is generally about 0.02 to about 10 mols, preferably about 0.05 to 5 mols, more preferably about 0.1 to 2 mols, of uracil (b) per mol of the 5-fluorouracil (a).

The anti-cancer compositions of this invention are useful for the treatment of cancers sensitive to 5-fluorouracil therapy in warm-blooded animals.

According to this invention, the 5-fluorouracil (a) and uracil (b) can be administered to warm-blooded animals individually in separate doses but are given preferably at the same time in the form of a single preparation. The anti-cancer compositions of this invention can be administered in the desired form of preparation in accordance with the therapy contemplated. They are provided for example as tablets, capsules and granules for oral administration or as parenteral solutions and suppositories for non-oral administration. These preparations can be formulated with use of carriers already known in the art.

Examples of useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. The amount of the 5-fluorouracil (a) in oral preparations may preferably be 10 to 200 mg per dosage unit. Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 100 mg of the 5-fluorouracil (a) per dosage unit. Suitable carriers for preparing suppositories are for example cacao butter, Witepsol-W35 (fat, trade mark of Dynamit Nobel A.G. of Germany). The suppositories may contain preferably 250 to 1000 mg of the 5-fluorouracil (a) per piece.

The results of biological applications and basic efficacy tests show that the preferred dose of the present anti-cancer compositions is usually about 0.5 to about 150 mg/kg, preferably about 0.5 to about 50 mg/kg calculated as the quantity of 5-fluorouracil. These values are in terms of the quantity per kilogram of the body weight of the warm-blooded animal per day.

PREPARATION 1

| | |
|---|---|
| Compound 1 | 250 mg |
| Uracil | 50 mg |
| Tris(hydroxymethyl)-aminomethane | 290 mg |
| Distilled water | (suitable amount) |
| | 5 ml (per ampule) |

PREPARATION 2

| | |
|---|---|
| Compound 1 | 100 mg |
| Uracil | 250 mg |
| Tris(hydroxymethyl)-aminomethane | 400 mg |
| Distilled water | (suitable amount) |
| | 5 ml (per ampule) |

Anti-cancer compositions of this invention are tested in cancer-bearing rats to determine the concentrations of 5-fluorouracil in the blood as well as in cancer tissues and to determine anti-cancer effects.

(1) Determination of concentrations of 5-fluorouracil in the blood and cancer tissues Ascites cells ($5 \times 10^6$) of AH-130 are subcutaneously transplanted in the armpit portion of male rats of Donryu strain weighing about 200 g. Seven days thereafter, the rats with cancer cells weighing at least 2 g are used, five rats in each group.

An anti-cancer composition comprising 5-fluorouracil (a) alone or in combination with uracil (b) in the proportion(s) listed in Table 1 is suspended in a 5% solution of gum arabic immediately before use, and the suspension is orally given to the animal at the listed dose. Two, four and eight hours after the administration, the blood serum and cancer tissue homogenate are collected, each of which is acidified with hydrochloric acid and extracted with chloroform. The resulting aqueous layer is examined for antibiotic activity according to the thin-cup method (Media Circle, Vol. 92, p. 259, 1967) with use of *Staphylococcus aureus* 209P strain. The results are given in Table 1 in terms of 5-fluorouracil concentration.

TABLE 1

| 5-Fluorouracil (a) | | Concentration of 5-fluorouracil (μg/ml) | | | | | |
|---|---|---|---|---|---|---|---|
| Compd. | Uracil (b) | In blood | | | in cancer tissues | | |
| No. | (m. mol/kg) | (m. mol/kg) | 2 hr | 4 hr | 8 hr | 2 hr | 4 hr | 8 hr |
| 1 | 0.08 | None | 0.11 | 0.02 | — | 0.34 | 0.16 | 0.05 |
| | | 0.08 | 0.55 | 0.03 | — | 0.72 | 0.43 | 0.18 |

(2) Determination of anti-cancer effects

Ascites cells ($5 \times 10^6$) of AH-130, are subcutaneously transplanted in the armpit of male Donryu rats weighing about 200 g (ten rats in each group). An anti-cancer composition comprising 5-fluorouracil (a) alone or in combination with uracil (b) in the proportion(s) listed in Table 2 is suspended in a 5% solution of gum arabic immediately before use. Twenty-four hours after the transplantation and during the following seven consecutive days the suspension is orally given to the animal once every day at the dose listed in Table 2. On the 10th day after the transplantation, the tumor is removed from the body and weighed to calculate the average weight (T) of the tumors in the group to which the composition has been given and the corresponding weight (C) in the control group to determine the ratio T/C. The results are listed in Table 2.

TABLE 2

| 5-Fluorouracil (a) | | Uracil (b) | Anti-cancer effect |
|---|---|---|---|
| Compd. No. | (m. mol/kg) | (m. mol/kg) | (T/C) |
| 1 | 0.08 | None | 0.69 |
| | | 0.16 | 0.32 |
| | | 0.08 | 0.59 |

The anti-cancer effect (T/C) achieved by the oral administration of 1 m. mol/kg of uracil (b) alone is 0.96.

Tables 1 and 2 reveal the following. When the 5-fluorouracil (a) is used conjointly with uracil (b), the 5-fluorouracil concentration remains almost at the same level in the blood but greatly increases in the cancer tissues and that the use of uracil (b) with any 5-fluorouracil (a) gives an increased anti-cancer effect. These results show that 5-fluorouracil (a) when used in combination with uracil (b), affords high anti-cancer effects in cancers sensitive to 5-fluorouracil therapy in warm-blooded animals synergically enhanced by the conjoint use of uracil (b).

(3) Compositions formulated according to Preparation 1 is tested by the foregoing method for anti-cancer effects on AH-130. Table 3 shows the results.

TABLE 3

| Prepn. No. | Method of administration | Components and dosage (mg/kg) | | Anti-cancer effect (T/C) | Anti-cancer effect* (control) (T/C) |
|---|---|---|---|---|---|
| 1 | I.v. | Compd. 1 | 10 | 0.30 | 0.66 |
| | | Uracil | 2 | | |

*Determined with use of compositions formulated in the same manner as above except that no uracil (b) is used.

(4) The anti-cancer compositions of this invention are tested in mice by the following methods to determine acute toxicity, anti-cancer effect and theapeutic index.

(a) Acute toxicity

Male mice of ICR strain weighing $22 \pm 1$ g are used, 5 mice in each group. 5-fluorouracil (a) and uracil (b) in the proportions listed in Table 5 are suspended in a 5% solution of gum arabic to prepare a suspension, which is forcibly orally administered to each mouse through a tube at a dose of 1 ml/100 g. Over the following period of three weeks the mice are checked every day for poisoning, body weight and mortality. The $LD_{50}$ is determined according to the up-and-down method 3 weeks after the administration. The results are given in Table 5.

(b) Anti-cancer effect

Tissues of sarcoma 180, $2 \times 10^6$, are subcutaneously transplanted in the back of male mice of ICR strain (6 mice in each group). 5-fluorouracil (a) and uracil (b) in the proportions listed in Table 5 are suspended in a 5% solution of gum arabic to prepare a suspension. Twenty-four hours after the transplantation and during the following seven consecutive days the suspension is orally given to the animal once every day. On the 10th day after the transplantation, the tumor is removed from the body and weighed to calculate the average weight (T) of the tumors in the group to which the composition has been given and the corresponding weight (C) in the control group to determine the ratio T/C. The effective dose (ED$_{50}$) for achieving 50% cancer inhibition is determined from the dose-response cure involving the dose and effect (T/C). The results are given in Table 4.

(c) Therapeutic index

The LD$_{50}$ and ED$_{50}$ values obtained above are used to determine the therapeutic index (LD$_{50}$/ED$_{50}$). The results are also listed in Table 4.

TABLE 4

| 5-Fluorouracil (a) (Compd. No.) | (b)/(a) mol ratio[1] | LD$_{50}$[2] (mg/kg) | ED$_{50}$[2] (mg/kg) | Therapeutic index (LD$_{50}$/ED$_{50}$) |
| --- | --- | --- | --- | --- |
| 1 | 0 | 115 | 18.5 | 6.2 |
|   | 2.5 | 115 | 8.5 | 13.5 |
|   | 10 | 97 | 6.0 | 16.2 |

[1]The mole ratio of uracil (b) to 5-fluorouracil (a).
[2]Expressed in terms of the amount (mg/kg) of 5-fluorouracil (a).

What is claimed is:

1. An anti-cancer composition for treating a cancer sensitive to 5-fluorouracil therapy in warm-blooded animals, said composition comprising a pharmaceutically effective amount of 5-fluorouracil and an effective amount of uracil, wherein about 0.2 to about 10 mols of uracil are present per mol of 5-fluorouracil.

2. Anti-cancer composition of claim 1 in the form of an oral preparation.

3. Anti-cancer composition of claim 1 in the form of a parenteral solution.

4. Anti-cancer composition of claim 1 in the form of a suppository.

5. A method of treating a cancer in a warm-blooded animal, wherein the cancer is sensitive to 5-fluorouracil therapy, said method comprising administering to the animal the composition of claim 1 in the form of a single preparation in an amount which is effective to deliver an anti-cancer amount of 5-fluorouracil to the cancer.

6. A method of treating a cancer in a warm-blooded animal, wherein the cancer is sensitive to 5-fluorouracil therapy, said method comprising administering to the animal 5-fluorouracil and uracil in separate doses, in an anti-cancer effective amount of 5-fluorouracil, wherein about 0.2 to about 10 mols of uracil are used per mol of 5-fluorouracil.

* * * * *